(12) United States Patent
Shao et al.

(10) Patent No.: US 8,851,010 B2
(45) Date of Patent: Oct. 7, 2014

(54) SYSTEMS AND METHODS FOR MEASURING, MONITORING AND CONTROLLING OZONE CONCENTRATION

(75) Inventors: ShouQian Shao, Fremont, CA (US); Jay DeDontney, Prunedale, CA (US); Jason Wright, Saratoga, CA (US)

(73) Assignee: Intermolecular, Inc., San Jose, CA (US)

( * ) Notice: Subject to any disclaimer, the term of this patent is extended or adjusted under 35 U.S.C. 154(b) by 454 days.

(21) Appl. No.: 13/271,471

(22) Filed: Oct. 12, 2011

(65) Prior Publication Data

US 2013/0091926 A1    Apr. 18, 2013

(51) Int. Cl.
| | |
|---|---|
| *G01F 1/76* | (2006.01) |
| *G01N 25/20* | (2006.01) |
| *G01N 33/00* | (2006.01) |
| *G01F 1/74* | (2006.01) |
| *G01N 25/18* | (2006.01) |
| *B05C 11/06* | (2006.01) |

(52) U.S. Cl.
CPC .............. *G01F 1/74* (2013.01); *G01N 33/0039* (2013.01); *G01N 25/18* (2013.01)
USPC ........ 118/663; 73/861.04; 73/25.01; 423/581

(58) Field of Classification Search
USPC .................... 73/25.01, 861.04; 118/663, 712; 423/581
See application file for complete search history.

(56) References Cited

U.S. PATENT DOCUMENTS

| | | | |
|---|---|---|---|
| 5,604,298 A | 2/1997 | Dosoretz et al. | |
| 5,904,170 A | 5/1999 | Harvey et al. | |
| 2007/0020160 A1* | 1/2007 | Berkman et al. | 422/186.14 |
| 2009/0162571 A1* | 6/2009 | Haines et al. | 427/569 |
| 2010/0119439 A1 | 5/2010 | Shindou | |

FOREIGN PATENT DOCUMENTS

WO    WO 2004027364 A1 *    4/2004    ............. G01K 13/02

* cited by examiner

*Primary Examiner* — Lisa Caputo
*Assistant Examiner* — Punam Roy

(57) ABSTRACT

Systems and methods to determine ozone concentration in a gas mixture of ozone and oxygen, based on measurements of the total gas mixture properties, can enable the measurements of ozone concentration at low pressure settings. The ozone concentration determination can be applied to vacuum processing chamber, using either novel ozone sensor or existing mass flow meter or controller.

12 Claims, 9 Drawing Sheets

SYSTEMS AND METHODS FOR MEASURING, MONITORING AND CONTROLLING OZONE CONCENTRATION

FIELD OF THE INVENTION

The present invention relates generally to determining a concentration of a gas in a gas mixture flow, and particularly related to determining ozone concentration in a gas mixture where ozone is generated from oxygen gas.

BACKGROUND OF THE INVENTION

Ozone has been widely used in semiconductor processing. For example, ozone can be used in combination with TEOS to deposit silicon dioxide. Ozone can be used in atomic layer deposition (ALD) process to form oxide films, such as aluminum oxide or hafnium oxide. Ozone can also be used for cleaning semiconductor wafers and semiconductor equipment, especially for removing hydrocarbon residues.

In general, an ozone generator is located a distance from the processing chamber, with the ozone concentration is measured at the output of the ozone generator. However, process windows have become narrower in advanced applications of both front end of line (FEOL) and back end of line (BEOL), especially in ALD, chemical vapor deposition (CVD) and interface treatment, and the ozone settling time between the ozone generator and the process chamber can cause the ozone concentration at the process chamber to be different from the desired level, leading to a compromised semiconductor product.

Thus, monitoring, measuring or controlling the ozone concentration at the point of use becomes critical. This has imposed additional requirements on ozone-related equipment, such as ozone generator and ozone concentration sensors. For example, in most applications the ozone is fed into a chamber where the pressure is under or around a few Torr range. However, there is no ozone sensor available to measure ozone concentration at such low pressure. For example, the available ozone sensors in the market which use UV absorption method, can only measure the ozone concentration above 8 PSI (405 Torr).

Therefore, ozone concentration sensors and controllers capable of operating at low pressure are needed.

SUMMARY OF THE DESCRIPTION

The present invention relates to systems and methods to determine a concentration of a gas in a gas mixture flow, such as the concentration of ozone in a mixture of ozone and oxygen, or the concentration of oxygen in a mixture of oxygen and nitrogen. The determination is based on a measurement of a thermal property of the gas mixture flow that is related to the mass of the gas mixture, such as the heat flux or the temperature gradient of the mixture flow through a sensing tube. The determination is further based on the fact that different gases in the gas mixture have different thermal properties, and thus a ratio of the different gases in the mixture can be calculated.

In some embodiments, the present invention discloses systems and methods to determine a concentration of a first gas generated from a converted portion of a second gas, forming a two-gas mixture comprising the first gas and the remaining portion of the second gas. The method comprises determining a mass flow rate of the second gas, and a thermal property of the gas mixture, and then calculating the concentration of the first gas through a difference in the thermal properties of the first gas and the second gas.

For example, to determine a concentration of ozone in a gas mixture of ozone and oxygen, a heat flux or a temperature gradient of the gas mixture flow is measured. An equation can be set up, equating the measured heat flux to the sum of the heat flux of the ozone flow and the heat flux of the oxygen flow. By knowing the total flow of the mixture, for example, by measuring the flow rate of the oxygen supply gas, the equation can be solved to provide the flows of ozone and oxygen, and the concentration of ozone with respect to the gas mixture.

In some embodiments, the present invention discloses systems and methods to determine a concentration of a first gas in a multiple-gas mixture comprising the first gas, a second gas, and one or more third gases, comprising subtracting the effect of the third gases from the gas mixture, and then calculating the concentration of the first gas based on the mixture of two gases.

For example, to determine a concentration of ozone in a gas mixture of ozone, oxygen, and nitrogen, a heat flux of the gas mixture flow is measured. Since the nitrogen flow is known, the flow and heat flux of ozone and oxygen can be determined, for example, by subtracting the nitrogen flow from the total flow, and by subtracting the nitrogen heat flux from the measured heat flux. The system is then equivalent to a two-gas mixture system, and the concentration of ozone can be calculated from the two-gas mixture formulation.

In some embodiments, the present invention discloses systems and methods for controlling a concentration using a measure concentration to control a generator until a desired concentration is achieved.

In some embodiments, the present invention discloses systems and methods to use an ozone concentration measurement system in a vacuum chamber system. A modified ozone concentration sensor can be used. Alternatively, existing mass flow meter or controller can be used, together with modification to a system controller to calculate the ozone concentration value.

BRIEF DESCRIPTION OF THE DRAWINGS

To facilitate understanding, identical reference numerals have been used, where possible, to designate identical elements that are common to the figures. The drawings are not to scale and the relative dimensions of various elements in the drawings are depicted schematically and not necessarily to scale.

The techniques of the present invention can readily be understood by considering the following detailed description in conjunction with the accompanying drawings, in which.

DETAILED DESCRIPTION

Figure 1A:
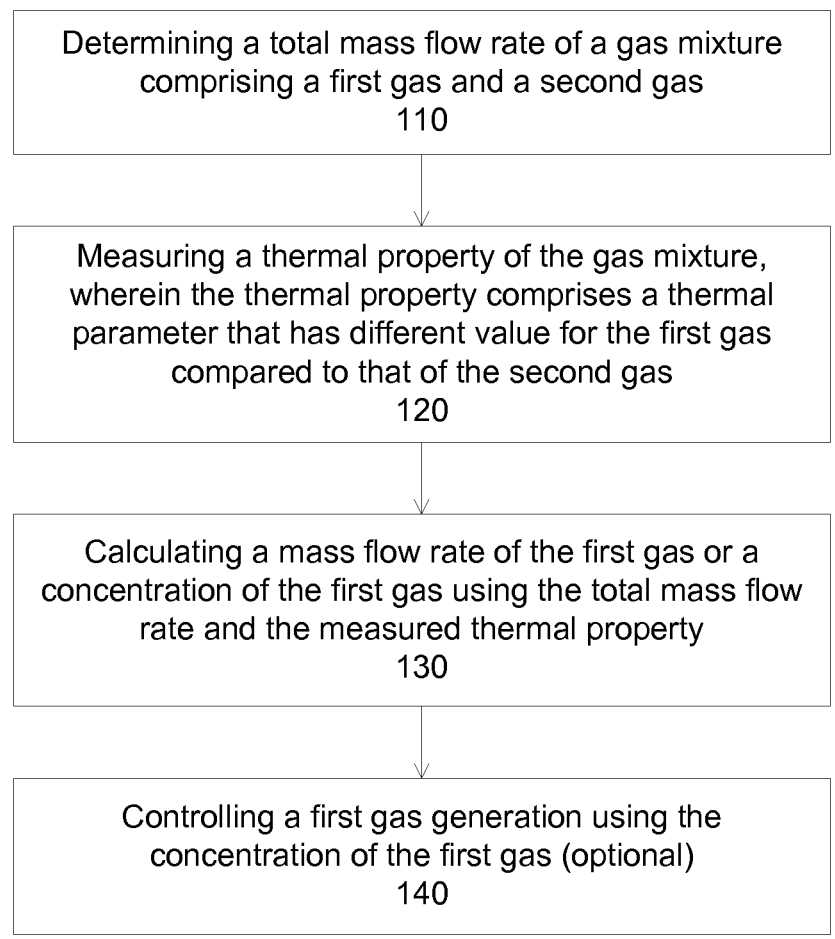
FIGS. 1A-1B illustrate exemplary flowcharts for determining individual mass flow rates or concentration in a gas mixture flow.

A detailed description of one or more embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to the embodiments has not been described in detail to avoid unnecessarily obscuring the description.

In some embodiments, the present invention discloses systems and methods to determine individual mass flow rates or concentration in a gas mixture from the data of the gas mixture. For example, by determining or measuring a flow rate and a heat flux (or temperature gradient) of the gas mixture, the present invention can provide individual flow rates or concentration of the gas components in the gas mixture. In some embodiments, the present methodology is based on the different behaviors of the individual gases in the gas mixture, which then enables the determination of the properties of the individual gases from the total gas mixture data. The gas mixture can be a mixture of two or more gases.

In some embodiments, the present invention discloses systems and methods to determine individual mass flow rates or concentration of a gas mixture generated from a supply gas. For example, an oxygen supply gas can produce a two-gas mixture of ozone and oxygen through an ozone generator, where ozone is generated from a converted portion of the oxygen supply gas and oxygen comprises the remaining portion. The following description describes the invention in the embodiments of ozone generated from oxygen, but the invention is not so limited, and can be applied to any gas mixture system.

Ozone can be generated using different generation methods such as corona discharge or ultraviolet light. Ozone concentration is calculated as the amount of ozone in the mixture of ozone and oxygen, expressed as a ratio of ozone and the mixture. Ozone concentration can be measured in pmol/mol (or ppm, parts per million)

$$C\left(\frac{\mu mol}{mol}\right) = \frac{\text{moles of ozone} \times 10^{-6}}{\text{moles of ozone} + \text{moles of oxygen}}$$

or weight percent (wt %)

$$C(\text{wt \%}) = \frac{\text{weight of ozone} \times 100}{\text{weight of ozone} + \text{weight of oxygen}}$$

The concentration of ozone typically ranges from 1 to 5 wt % in air and from 6 to 20 wt % in oxygen.

In an ozone generator, oxygen is converted to ozone as followed:

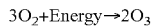

Some catalyst can also be added to the generator, for example, a small amount of nitrogen can improve the efficiency of an ozone generator

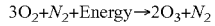

In some embodiments, the present invention discloses determining an ozone concentration based on a thermal property of the gas mixture.

In a single gas flow, the gas flow rate can be calculated based on a measurement of heat flux or temperature gradient of the gas flow. The measured value is converted to the mass flow rate through the specific heat. For example, the heat flux q of a flowing gas relates to its mass flow rate F and the specific heat $C_p$:

$$q = h\Delta T = kFC_p$$

where h is the heat transfer coefficient, $\Delta T$ is the temperature gradient, and k is a proportional constant.

In practice, by measuring a drop in temperature $\Delta T$, for example, when the gas is flowing in a sensing tube, the mass flow rate F can be calculated, using the specific heat value $C_p$ for the particular gas. The specific heat is directly related to the mass (and other physical parameters) of the gas molecules, and is well known for many gases, thus provides a convenient way to determine mass flow rates in single gas flow systems. This is the operating principle for mass flow meter or controller, employing measurements of a temperature gradient to enable calculation of mass flow rate.

In some embodiments, the present invention discloses systems and methods to measure mass flow rates or concentrations of individual gases in a two-gas mixture flow, utilizing thermal properties and thermal parameters of the individual gases. In some embodiments, the thermal properties and the thermal parameters are the heat flux and the specific heats of the gas components in the gas mixture, respectively.

For a mixture flow of a first gas flow $F_1$ having specific heat $C_{p1}$ and a second gas flow $F_2$ having specific heat $C_{p2}$, a measured heat flux q for the gas mixture is $$q = kF_1C_{p1} + kF_2C_{p2} = k(F_1C_{p1} + F_2C_{p2}) \quad \text{(Eqn 1)}$$

This heat flux equation has two unknowns $F_1$ and $F_2$, and therefore in some cases requires a second equation to determine the individual flow rates. For example, by knowing the total flow rate (e.g., the flow rate $$F = F_1 + F_2 \quad \text{(Eqn 2)}$$

of the gas mixture), the individual flow rates or the concentration in a two-gas mixture system can be determined through the system of linear equations (Eqns 1 and 2). The total flow rate can be measured by a mass flow meter or controller at the supply gas, since it is more difficult to perform measurements at the gas mixture.

In some embodiments, additional requirements can be imposed, for example, the thermal parameters (e.g., the specific heats $C_{p1}$ and $C_{p2}$) of the individual gases are distinguished from each other, in order to create a system of linear independent equations.

The individual flow rates $F_1$ and $F_2$ and concentration C in a mixture are related, and can be calculated from each other, thus the following description mainly describes measuring and controlling concentration, but the invention is not so limited, and can be equally applied to measuring and controlling individual flow rates. For example, the mass concentration C in weight percent of the first gas in a two-gas mixture can be calculated as followed:

$$C=100 F_1/(F_1+F_2)$$

FIG. 1A illustrates an exemplary flowchart for determining individual mass flow rates or concentration in a gas mixture flow according to some embodiments of the present invention. By determining a mass flow rate of a supply gas which is converted to a gas mixture, together with a thermal property (such as the heat flux) of the gas mixture, the flow rates of individual gases in the mixture, and consequently the mass concentration of an individual gas in the mixture, can be calculated. The thermal property is selected to be related to distinguished thermal parameters (such as specific heat) of the individual gases in the mixture.

In operation 110, a total mass flow rate of a gas mixture is determined. The gas mixture can be a two-gas mixture, such as a mixture of ozone and oxygen, or a mixture of oxygen and nitrogen. The gas mixture can be a multiple-gas mixture, having three or more individual gases such as a mixture of ozone, oxygen, and nitrogen. The total mass flow rate is the sum of the flow rates of all individual gases in the gas mixture.

In some embodiments, the total mass flow rate can be determined by measuring the flow rate of the supply gas, such as at an inlet of an ozone generator. For example, a mass flow meter can be coupled to an input oxygen supply gas conduit to measure the total mass flow rate of the gas mixture. In some embodiments, the total mass flow rate can be determined by setting the flow rate of the mixture, such as at an inlet or outlet of a flow rate or concentration measurement system. For example, a mass flow controller can be coupled to a gas mixture conduit to set the total mass flow rate of the gas mixture.

In operation 120, a thermal property of the gas mixture is measured. The thermal property is selected to be related to a thermal parameter that has distinguished values for at least two of the individual gases in the gas mixture. The thermal property is preferably heat flux or temperature gradient. The thermal parameter is preferably specific heat, which is directly related to the mass of the flowing gases and is different for different gases.

In operation 130, the individual mass flow rates or the concentration can be calculated using the total mass flow rate and the measured thermal property (such as the heat flux or temperature gradient). The thermal parameters (such as the specific heat) of the first and second gases can be determined, and can be incorporated into the calculation as constant factors. Other forms of the thermal parameters can be used, such as conversion factors, comparing the specific heat of different gases to the specific heat of nitrogen.

Different methods to calculate the individual mass flow rates or the concentration are within the scope of the present invention. For example, the calculation can be based on a formula linking an assumed or fictitious flow rate and the total mass flow rate. The assumed flow rate can be calculated from a measured heat dissipation of the total mass flow rate together with an assumption that the gas mixture comprises only the first gas or the second gas. Since the specific heats of the first and second gases are different, one of the assumed flow rates for the first and second gases is larger and one smaller than the total (e.g., actual) mass flow rate. An advantage of using the fictitious flow rate is the ability to use a conventional mass flow meter or controller. The formula linking the concentration to the assumed flow rate and the total flow rate comprises a difference between the two flow rates, and specifically comprises a ratio of the difference to the total flow rate.

Alternatively, the individual mass flow rates or the concentration can be calculated based on a formula linking the total mass flow rate and an effective specific heat of the gas mixture. For example, the effective specific heat Cp can be calculated based on a ratio of the two gas flows, such as $$(F_1+F_2)C_p=F_1C_{p1}+F_2C_{p2}$$

In some embodiments, the concentration Y of the first gas can be calculated from the following formula:

$$Y=c(X-Z)/X$$

where X is the total mass flow rate, Z is the measured mass flow rate assuming the flow only contains the second gas, and c is a constant. This approach can be used for existing mass flow meters or controllers, which are calibrated with a specific constant value. For example, a mass flow meter or controller can be calibrated to measure oxygen flow by setting the conversion factor to that of oxygen. The mass flow reading is then correct for oxygen flow, and differs for other gases.

By using the above formula, the mass flow meter or controller can be calibrated to the second gas, presenting the reading Z. The concentration of the first gas can be calculated from this reading.

In some embodiments, the present invention discloses systems and methods to control a concentration, where the calculated concentration value can be used to achieve a desired concentration setting, for example, by adjusting a gas generation system according to the concentration reading. In operation 140, the concentration of the first gas can be used to control a first gas generation system to achieve a desired or setting concentration value.

For example, the concentration measurement can be applied to an ozone/oxygen mixture where the ozone is generated from an ozone generator. To achieve a desired ozone concentration, the power of the ozone generator can be dynamically adjusted with feedback from the measured ozone concentration.

Figure 1B:
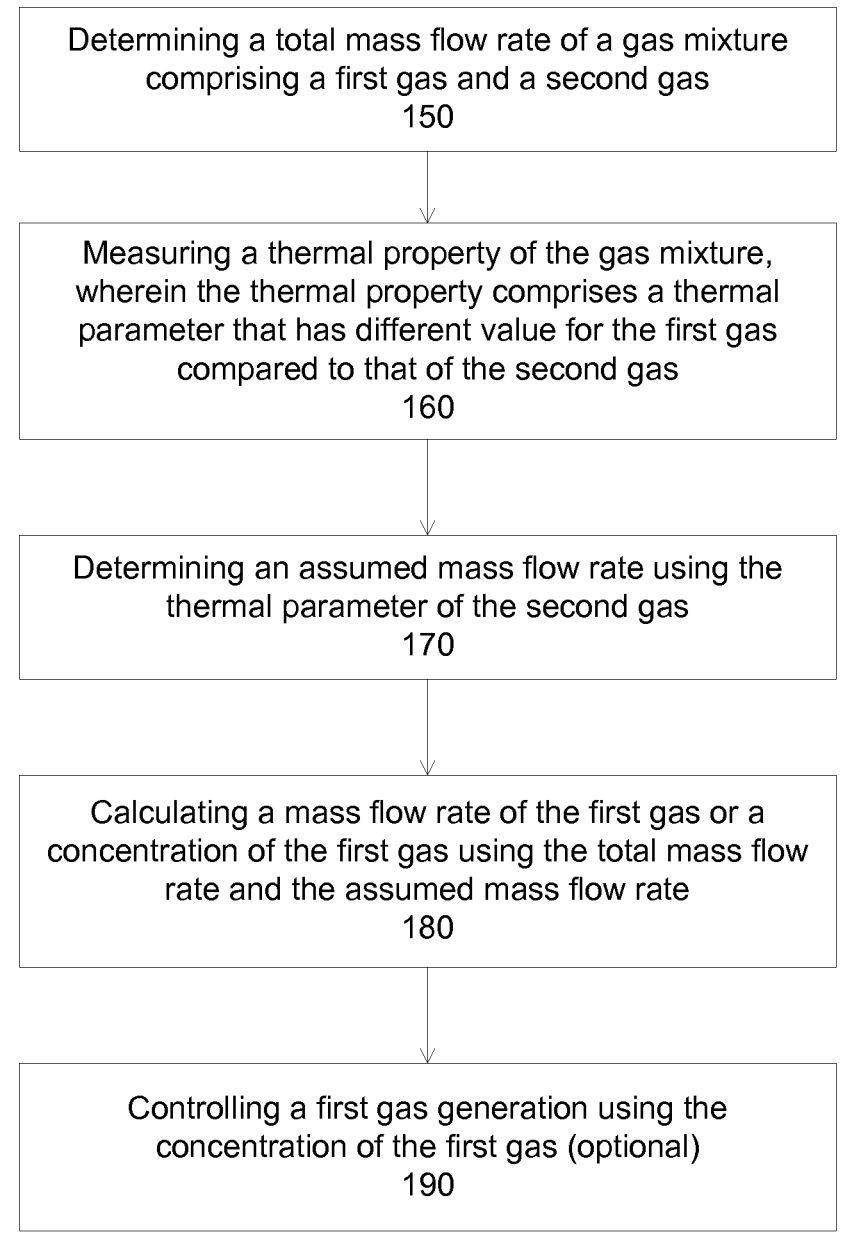

FIG. 1B illustrates an exemplary flowchart for determining individual mass flow rates or concentration in a gas mixture flow using an existing measuring device according to some embodiments of the present invention. By setting the measuring device, for example, a mass flow meter or controller, for the conversion factor of the second gas, the measuring device can return an assumed flow rate, meaning a flow value that is correct only if the flowing gas is the second gas. Using a second conversion factor c, the concentration for the first gas can be calculated using the assumed flow rate and the total flow rate.

In operation 150, a total mass flow rate of a gas mixture is determined, for example, by measuring a mass flow rate of the supply gas. In operation 160, a thermal property of the gas mixture is measured, which is preferably the heat flux or the temperature gradient.

In operation 170, the measuring device is calibrated for a certain gas, and thus returns an assumed mass flow rate. For example, a mass flow meter or controller is set using the conversion factor (e.g., based on the specific heat) for the second gas. The assumed mass flow rate is the actual mass flow rate if the gas is the second gas.

In operation 180, the individual mass flow rates or the concentration can be calculated using the total mass flow rate and the assumed mass flow rate. For example, the concentration Y of the first gas can be calculated from the formula Y=c(X−Z)/X where X is the total mass flow rate, Z is the assumed mass flow rate, and c is a conversion factor.

In operation 190, the concentration of the first gas can be used to control a first gas generation system to achieve a desired or setting concentration value.

In some embodiments, the present invention discloses systems and methods to determine a concentration of ozone in an ozone/oxygen mixture where the ozone is generated from the oxygen gas. Alternatively, the present invention can also determine individual flow rates or concentration of two separate gases, such as oxygen and nitrogen.

Other variations are also within the scope of the present invention. For example, instead of determining a total flow rate, the flow rate of the first or second gas can be determined separately, which is then used to determined the concentration.

Figure 2A:
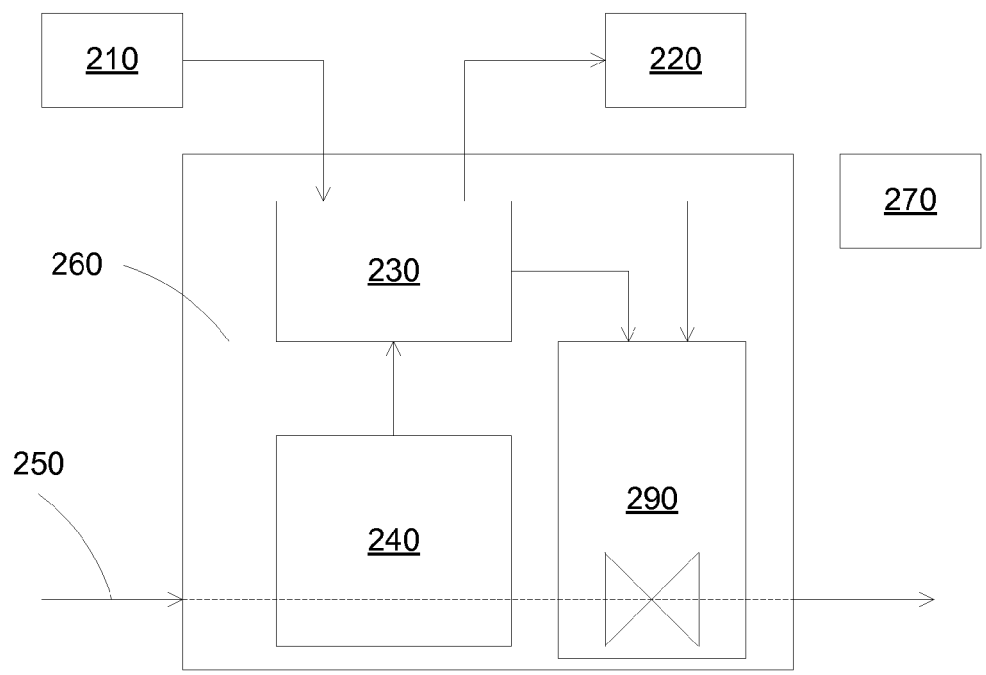
FIGS. 2A-2B illustrate exemplary system configurations for concentration determination.
Figure 2B:
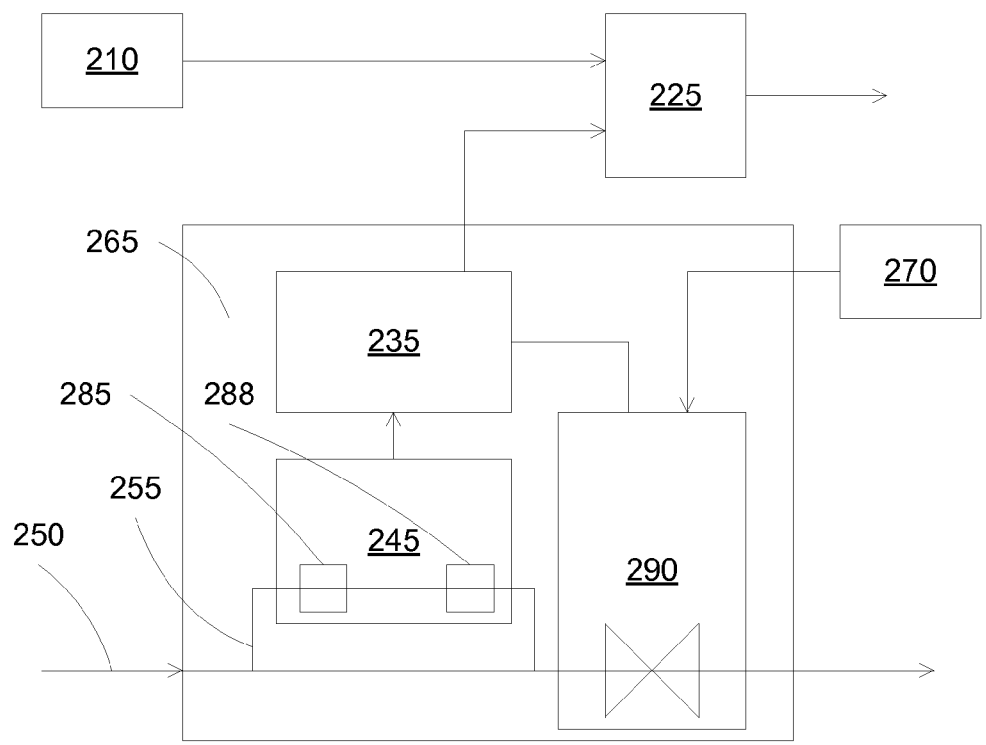

FIGS. 2A-2B illustrate exemplary system configurations for concentration determination according to some embodiments of the present invention. Novel devices or existing devices can be used.

In FIG. 2A, a controller device 260 is coupled to a flow conduit 250 which carries a flow mixture comprising a first and a second gas. A measuring component 240 is coupled to the conduit (or a bypass line from the conduit) to measure a thermal property (such as a heat flux or a temperature gradient) of the flow mixture. The result is supplied to a controller 230, which also accepts a second input 210, for example, a total mass flow rate through the conduit 250. The controller calculates and returns 220 the individual mass flow rates or a concentration of the first gas in the mixture. These portions of the controller device 260 act as a meter, such as a concentration meter for measuring the concentration value.

The flow rate through the conduit 250 can be controlled by a valve system 290, which accepts an input setting value 270 and a measured value from controller 230, such as the total flow 210, the individual flow rates or the concentration 220. The valve system 290 is regulated until the flow rate through the conduit 250 matches the setting value 270.

In some embodiments, controller 260 represents an exemplary ozone sensor according to some embodiments of the present invention. Ozone sensor 260 accepts an ozone mixture flow 250 and a total flow signal 210, and outputs a signal 220, representing the ozone concentration in the ozone mixture 250. The ozone sensor 260 can be further used as a flow controller, accepting a flow setting 270 to regulate the ozone mixture flow 250.

In FIG. 2B, a controller device 265 is coupled to a conduit 250 with valve system 290 regulating the conduit flow. In some embodiments, controller 265 represents another exemplary ozone sensor according to some embodiments of the present invention. A bypass line 255 is branched from the conduit 250, coupled to two temperature sensors 285 and 288 to measure a temperature difference in the bypass line 255. Other components, such as a heater can be included in the circuit 245 to facilitate the measurement. The temperature difference value is supplied to a controller 235, and can be converted to a mass flow value. The controller device 265 can be an existing mass flow controller, and in that case, only suitable for measuring a single gas flow, or a gas mixture with known components.

In some embodiments, the output of the controller 235 and the total mass flow rate 210 are supplied to a calculation device 225, where the concentration can be calculated. The calculation device 225 can be integrated with the controller device 265, or can be a separate entity. The calculation device 225 can be integrated to other devices, such as a system controller to control and regulate multiple devices, including the controller device 265.

Figure 3:
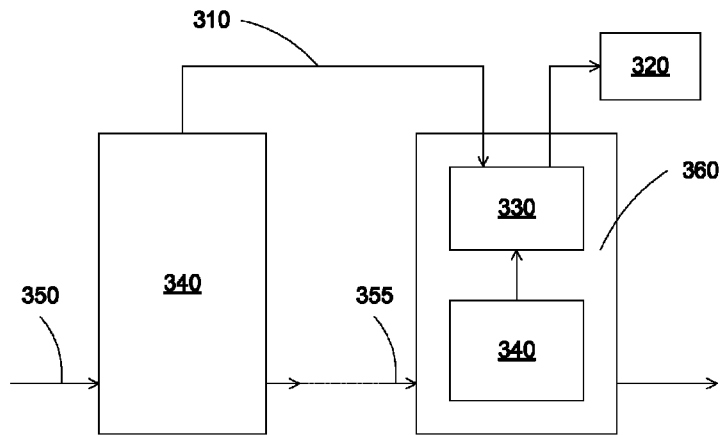
FIG. 3 illustrates an exemplary concentration measurement.

FIG. 3 illustrates an exemplary concentration measurement according to some embodiments of the present invention. The systems show measurement devices 360, but controller devices, such as controller device 260, can be used.

Measurement device 360 comprises measuring component 340 to measure a thermal property of the flow in conduit 355, and controller 330 to calculate a concentration value 320 in the gas mixture. The total mass flow rate is measured separately from another mass flow meter or controller device 340, and supplied to the measuring device 360. The device 340 can be a standard mass flow meter or controller, coupled to the conduit 350 to measure a supply gas for the mixture flow.

In some embodiments, measurement device 360 represents an exemplary ozone sensor according to some embodiments of the present invention. Ozone sensor 360 accepts an ozone mixture flow 355 and a total flow signal 310, and outputs a signal 320, representing the ozone concentration in the ozone mixture 355.

Figure 4:
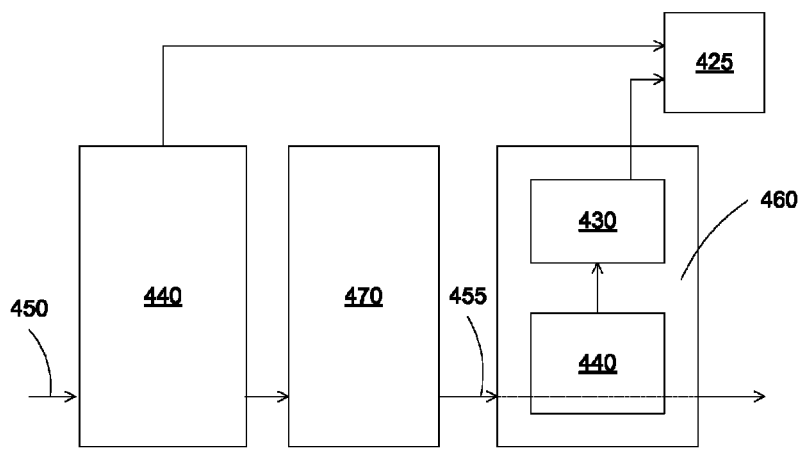
FIG. 4 illustrates an exemplary ozone concentration measurement according to some embodiments of the present invention.

FIG. 4 illustrates an exemplary ozone concentration measurement according to some embodiments of the present invention. The systems show an existing measurement device, such as a meter device 460 (e.g., a mass flow meter), but existing controller devices or novel meters or controllers according to the present invention can also be used.

Conduit 450 supplies oxygen to an ozone generator 470, which outputs a gas mixture of ozone and oxygen. Depending on the power of the generator 470, the concentration of ozone in the gas mixture can be changed. However, the total mass of ozone and oxygen in the gas mixture is constant, and equal to the input oxygen flow in conduit 450. The total mass flow rate, e.g., the mass flow rate of oxygen before the ozone generation, is measured by meter device 440, which provides an output to controller 425. The gas mixture flow 455 enters and is measured by the measurement device 460, which provides an output to controller 425. The output can be raw data, such as the temperature gradient, or converted data, such as an assumed flow rate. The controller 425 then calculates the concentration of ozone in the gas mixture, based on the total mass flow rate (from device 440) and the mixture flow rate (from device 460). Parameters for oxygen and ozone can be stored in either device 460 or controller 425 to enable the concentration calculation. Measurement device 360 can comprise measuring component 440 to measure a thermal property of the flow in conduit 455, and controller 430 to calculate a concentration value in the gas mixture.

In some embodiments, measurement device 460 together with the controller 425 (or a portion that performs the ozone concentration calculation) represents an exemplary ozone sensor according to some embodiments of the present invention. Measurement device 460 can be an existing mass flow meter, with a conversion factor set to any gas, preferably oxygen. Controller 425 can be a standalone controller, performing the ozone concentration calculation. The controller 425 can be integrated with other controller, such as a system controller.

In some embodiments, the present invention discloses systems and methods to control a concentration, such as controlling an ozone concentration from an ozone generator. For example, an ozone concentration is measured, and the measured ozone concentration is fed back to the ozone generator to adjust an ozone generation capability, such as power, until the desired ozone concentration is achieved.

Figure 5A:
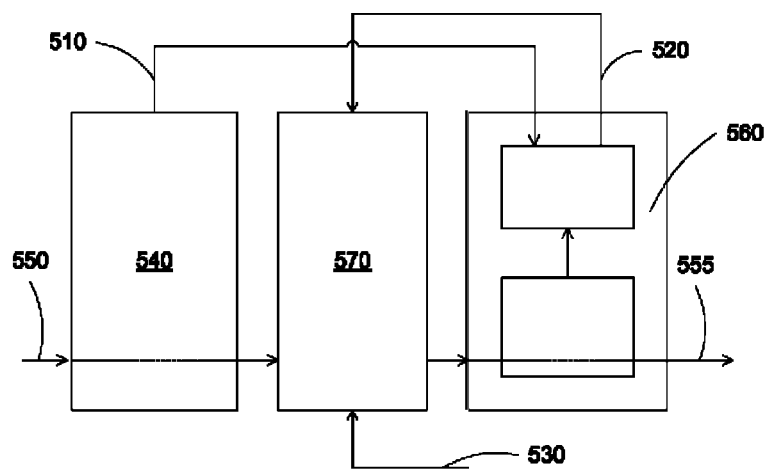
FIGS. 5A-5B illustrate exemplary configurations for controlling a concentration.
Figure 5B:
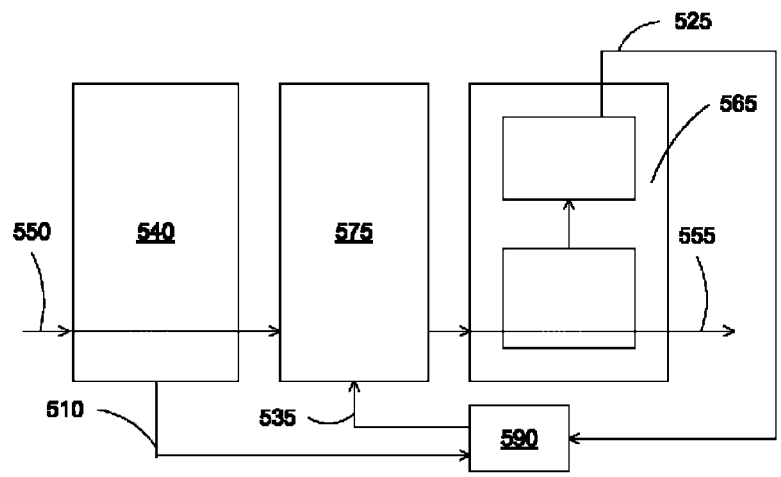

FIGS. 5A-5B illustrate exemplary configurations for controlling a concentration according to some embodiments of the present invention. The concentration control can be performed by the generator or by an external controller.

In FIG. 5A, a generator, such as an ozone generator 570 is coupled to an oxygen flow 550 to deliver a mixture flow 555 of ozone and oxygen. The ozone concentration in the mixture flow 555 is measured by the present ozone sensor 560, such as ozone sensor 360, operated as described above in some embodiments. The mixture flow 555 is shown after the ozone sensor 560, but the same mixture flow is also at the input to the ozone sensor 560, since the ozone sensor 560 does not affect the ozone mixture during the ozone concentration measurement. A gas flow meter 540 is coupled to the oxygen flow 550 to measure a total gas flow 510, which is then supplied to the sensor 560 to help determining the ozone concentration 520. The measured ozone concentration 520 is supplied to the ozone generator 570, and compared to an ozone setting 530. The power of the ozone generator 570 can be adjusted accordingly so that the measured ozone concentration 520 matches the ozone concentration setting 530.

In FIG. 5B, a controller 590 performs the regulation of the ozone concentration, receiving a measurement 525 from the ozone sensor 565 (operated similar to ozone sensor 365) and the total flow 510 from the gas flow meter 540 to calculate an ozone concentration. The calculated ozone concentration can be compared with a desired ozone concentration, and a power setting 535 can be delivered to the ozone generator 575 to adjust the amount of generated ozone. In this configuration, an existing mass flow meter can be used in place of the ozone meter 565 to provide an assumed flow rate to the controller 590. In addition, an ozone generator with a power adjustment circuit can be used.

In some embodiments, one or more third gases can be included in the gas flow mixture, for example, to dilute the mixture or to perform some other functions. For example, an ozone generator can accept a small flow of nitrogen, in addition to the oxygen flow, to improve the performance such as the ozone generation ability. In this case, the gas flow mixture comprises ozone, oxygen and nitrogen.

In some embodiments, the present invention discloses systems and methods to measure and control individual gas flow rates or concentrations in a flow mixture comprising more than two elements. In some embodiments, the process is performed by removing the effects of the third gases, effectively reducing the multiple-gas mixture system into a two-gas mixture system. In other embodiments, a comprehensive calculation can be used, setting and solving a system of linear equations involving all gases. The present description describes some approaches, but variations are also within the scope of the present invention.

In some embodiments, the present invention discloses methods to determine a concentration of a first gas in a gas mixture comprising the first gas and a second gas. An exemplary method comprises measuring a total mass flow rate of the gas mixture, measuring a thermal property of the gas mixture flow, wherein the thermal property comprises a thermal parameter that has a different value for the first gas compared to that of the second gas, and calculating a concentration of the first gas using the total mass flow rate and the measured thermal property. The thermal property can comprise a heat flux or a temperature gradient of the gas mixture flow, and the thermal parameter can comprise the specific heat. In some embodiments, the method determines the concentration of ozone in a mixture of ozone and oxygen, with the first gas comprising ozone and the second gas comprising oxygen.

In some embodiments, determining a total mass flow comprises measuring an oxygen mass flow rate before being converted to ozone, or setting an oxygen mass flow rate before being converted to ozone.

In some embodiments, the concentration of ozone is calculated by calculating an assumed mass flow rate for ozone using the thermal property of the gas mixture flow and the thermal parameter of oxygen, and then determining the concentration of ozone based on the assumed mass flow rate and the total mass flow rate. The mixture can further comprise nitrogen with a known flow rate, and wherein the concentration of ozone is calculated by using a total flow rate of the mixture minus the flow rate of nitrogen, and a measured total thermal property for the mixture minus a thermal property for nitrogen.

In some embodiments, the present invention discloses a method to control a desired concentration using a concentration sensor, comprising delivering a signal representing the determined concentration of the first gas to one of a first gas generation, and regulating the one of a first gas generation and a second gas generation to achieve the desired concentration based on the signal. In some embodiments, the method regulates the generation of ozone from oxygen with the first gas comprising ozone and the second gas comprising oxygen.

Figure 6:
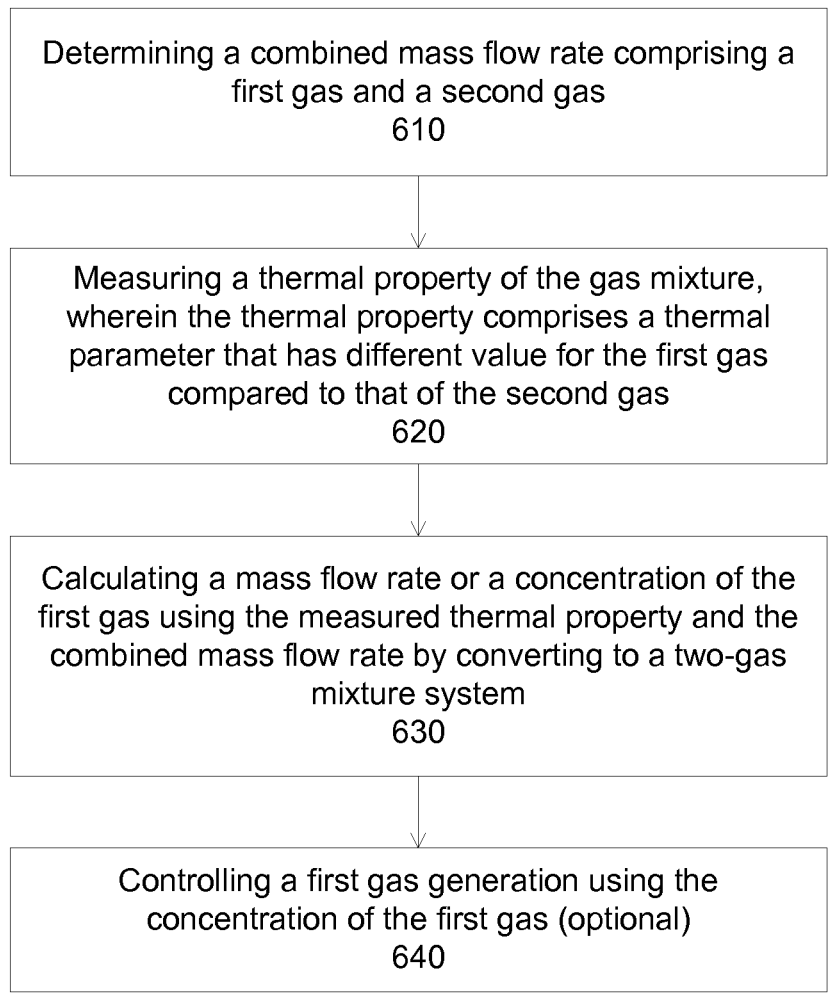
FIG. 6 illustrates an exemplary flowchart for determining individual mass flow rates or concentration in a multiple-gas mixture flow.

FIG. 6 illustrates an exemplary flowchart for determining individual mass flow rates or concentration in a multiple-gas mixture flow according to some embodiments of the present invention. The multiple-gas mixture comprises a first gas, a second gas, and one or more third gases. In some embodiments, the third gases are known, and thus their effects can be removed from the calculations.

In operation 610, a combined mass flow rate comprising the first gas and the second gas is determined. The combined mass flow rate can be determined from a measurement of the first and second gas flows, or from a measurement of the total gas flow subtracting the third gases. By removing the third gases, the process is set up for a two-gas mixture calculation.

In operation 620, a thermal property, such as heat flux or temperature gradient, of the total gas mixture is measured. The measured value is typically related to the total mixture, since all gases are well mixed in the gas mixture.

In operation 630, a mass flow rate of a concentration of the first gas is calculated by converting the system to a two-gas mixture system. For example, the thermal property of the third gases is subtracted from the measured thermal property to get a thermal property for only the first and second gases. With the total mass flow rate of the first and second gases already determined, calculations based on a two-gas mixture system can be performed, using any process described above, to determine the individual flow rates of the first and second gases. Operation 640 optionally controls a first gas generation using the measured concentration of the first gas.

The concentration can be determined from the individual flow rates, depending on the applications. For example, an ozone concentration in weight percent of ozone with respect to the mixture of ozone of oxygen can be calculated, with the nitrogen third gas ignored.

$$C(\text{wt }\%) = \frac{100 \times \text{Ozone mass flow rate}}{\text{Ozone mass flow rate} + \text{Oxygen mass flow rate}}$$

Alternatively, an ozone concentration in weight percent of ozone with respect to the total mixture of ozone, oxygen, and the nitrogen third gas can be used.

$$C(\text{wt \%}) = \frac{100 \times \text{Ozone mass flow rate}}{\text{Ozone mass flow rate} + \text{Oxygen mass flow rate} + \text{Nitrogen mass flow rate}}$$

Figure 7A:
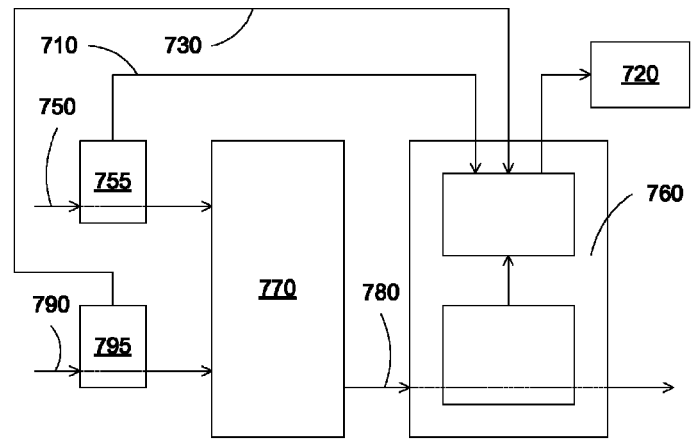
FIGS. 7A-7B illustrate multiple-gas mixture configurations according to some embodiments of the present invention.
Figure 7B:
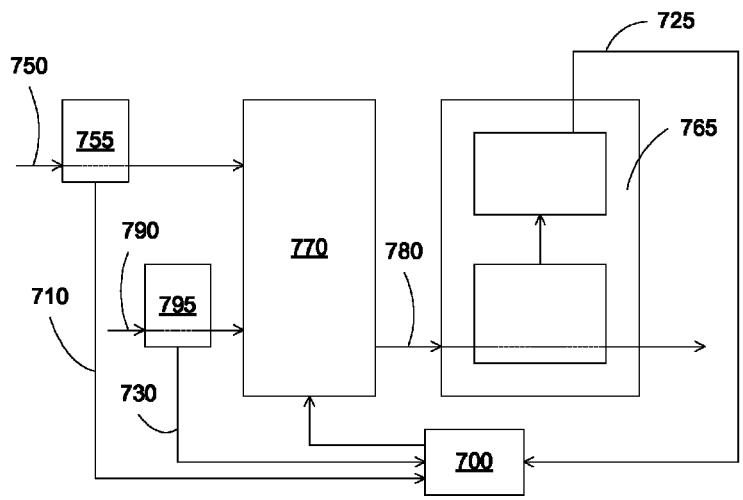

FIGS. 7A-7B illustrate multiple-gas mixture configurations according to some embodiments of the present invention. In FIG. 7A, an ozone generator 770 is coupled to an oxygen flow 750 and a nitrogen flow 790 to deliver a mixture flow 780 of ozone, oxygen and nitrogen. The ozone concentration in the mixture flow 780 is measured by the present ozone sensor 760, which operates similar to ozone sensors 360 and 460 described above, with the exception of receiving two flow input signals 710 and 730. A gas flow meter 755 is coupled to the oxygen flow 750 to measure a combined gas flow 710 (comprising the mixture of ozone and oxygen in the total mixture flow 780), which is then supplied to the ozone sensor 760. A gas flow meter 795 is coupled to the nitrogen flow 790 to measure a nitrogen gas flow 730, which is then also supplied to the ozone sensor 760. Knowing the nitrogen flow rate 630, the ozone sensor 760 can remove the effect of nitrogen on the measured value, and then calculate the ozone concentration based on a mixture of ozone and oxygen.

In some embodiments, the present invention discloses an ozone sensor, such as ozone sensor 760, accepting an ozone mixture flow 780 and two or more flow signals 710 and 730, and outputs a signal 720, representing the ozone concentration in the ozone mixture flow 780.

In FIG. 7B, a controller 700 performs the calculation of ozone concentration, receiving a measurement 725 from the ozone sensor 765, the combined flow 710 from the gas flow meter 755, and the nitrogen flow 730 from the gas flow meter 795 to calculate an ozone concentration. In this configuration, an existing mass flow meter can be used in place of the ozone sensor 765 to provide an assumed flow rate to the controller 700.

In some embodiments, the present invention discloses gas concentration sensors to determine a concentration of a first gas in a mixture comprising the first gas and a second gas. An exemplary gas concentration sensor comprises an inlet port and an outlet port for the gas mixture flow; a sensor assembly coupled to the inlet port to measure a thermal property of the gas mixture flow, wherein the thermal property comprises a thermal parameter that has a different value for the first gas compared to that of the second gas; an electrical port to accept a flow signal related to the mass flow rate of the first gas and the second gas; and a controller coupled to the sensor assembly to accept an output of the sensor assembly, the controller further coupled to the electrical port to accept the flow signal, the controller configured to produce a signal related to the concentration of the first gas. The thermal property can comprise a heat flux or a temperature gradient of the gas mixture flow. The thermal parameter can comprise the specific heat.

In some embodiments, the gas concentration sensor determining the concentration of ozone in a mixture of ozone and oxygen with the first gas comprising ozone, and the second gas comprising oxygen. The gas concentration sensor can further comprises a mass flow meter to measure the flow of the gas mixture flow, and wherein an output of the mass flow meter is coupled to the electrical port. The mixture can further comprise nitrogen with a known flow rate, wherein the flow signal comprises a mass flow rate of ozone and oxygen; and wherein the controller is further configured to convert the thermal property of the total gas mixture to the thermal property of ozone and oxygen.

In some embodiments, the concentration sensor further comprises a feedback circuit to provide the concentration signal to an ozone generator; and a power output based on a difference between the concentration signal and a desired concentration to regulate the ozone generator.

In some embodiments, the present invention discloses a processing system comprising a gas concentration sensor and a vacuum process chamber, wherein the outlet port for the gas mixture flow is disposed in a vicinity of the vacuum process chamber. The controller is further coupled to the vacuum process chamber to operate the vacuum process chamber.

In some embodiments, the present invention discloses an ozone sensor that can operate at a wide pressure range, such as the pressure ranges suitable to conventional mass flow meters or controllers. In addition, the present systems can measure ozone concentration at low pressure ranges, such as less than 400 Torr, preferably less than 100 Torr, and more preferably less than 10 Torr. This low pressure operation offers significant advantages over prior art ozone sensors, which typically can perform measurements at pressures higher than 400 Torr. For example, existing ozone sensors are based on infrared absorption, and thus require a minimum amount of ozone molecules to have measurable absorption signals.

In some embodiments, the present invention discloses an ozone sensor capable to connecting to a vacuum processing chamber where the operating pressure is less than a few hundred Torr, and typically less than a few Torr. The present ozone sensor can be installed at point of use to enable measuring or monitor the level of ozone in a process chamber.

In some embodiments, the present ozone sensor can include a conventional mass flow meter or a mass flow controller, with additional hardware or software to determine an ozone concentration from two inputs (such as a total flow rate and a measured heat flux of the total flow). The hardware or software can be integrated to the conventional mass flow meter or a mass flow controller, or can be coupled to a system controller.

In some embodiments, the present invention discloses a process chamber utilizing the present ozone sensor. The process chamber can be configured for application using ozone, such as TEOS/Ozone deposition, or ALD processes. Many ALD systems use ozone as an oxidant for film deposition, such as $Al_2O_3$, $HfO_2$, $ZrO_2$, $Ta_2O_5$ and $TiO_2$. The ozone generator usually is located far away from the process chamber, and the ozone concentration is measured at ozone generator output. The long delivery line, which can be heated, can affect the ozone concentration, for example, some ozone could be lost before reaching process chamber. Measuring, monitoring or controlling the ozone concentration at a point of use is therefore important for critical process control.

In some embodiments, the present invention discloses hardware and process monitoring, troubleshooting as well as controlling, comprising positioning an ozone sensor in a close vicinity of a process chamber, and configuring the system controller to accept the operation of the ozone sensor.

Figure 8:
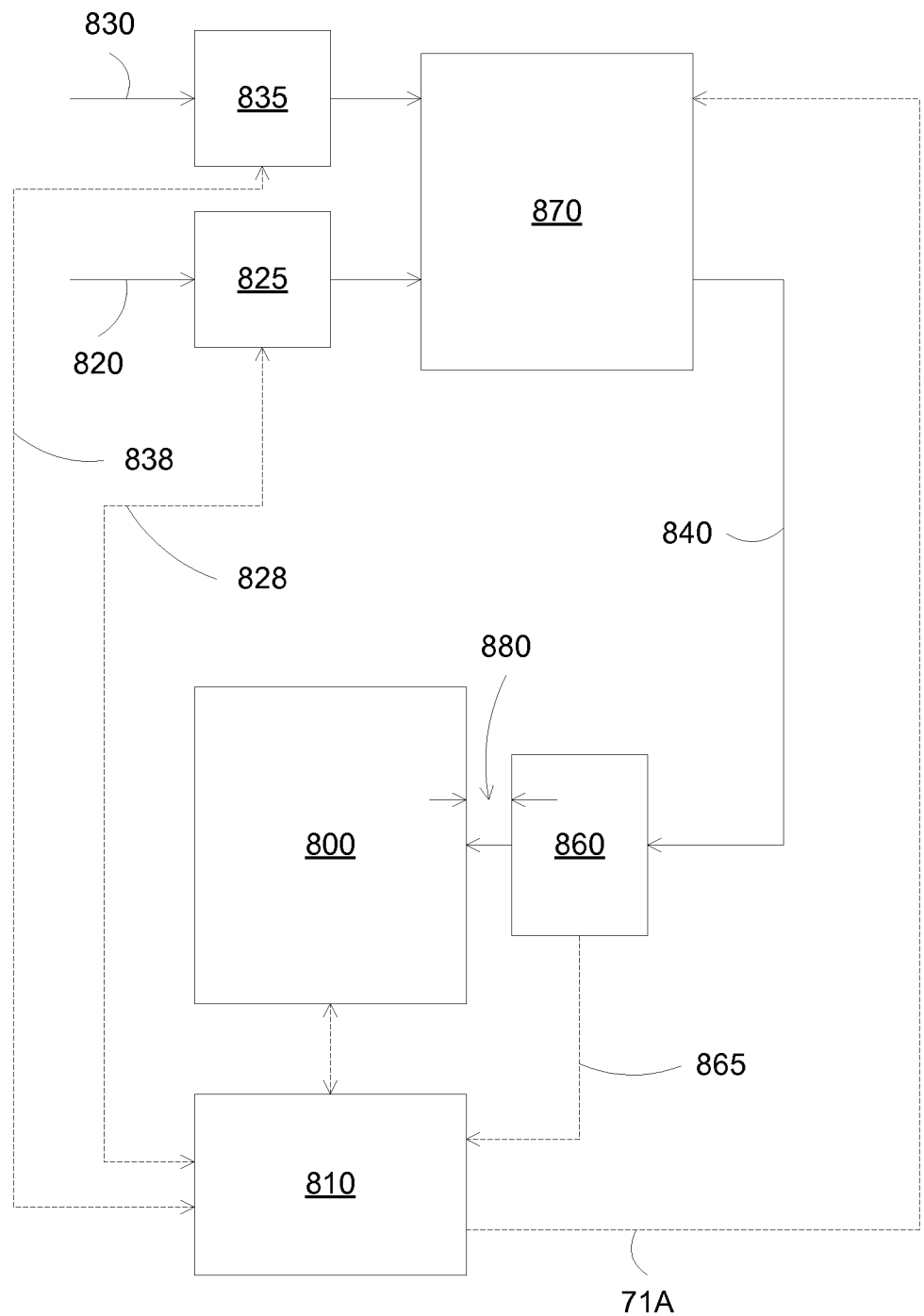
FIG. 8 illustrates an exemplary configuration for a process chamber utilizing an ozone sensor.

FIG. 8 illustrates an exemplary configuration for a process chamber utilizing an ozone sensor according to some embodiments of the present invention. A process chamber 800 is controlled by a system controller 810, for example, to heat a substrate support, to transfer substrates in and out of the process chamber, or to control process gases and pressure in the process chamber. An ozone generator 870 accepts an oxygen input flow 820 and a nitrogen input flow 830, and outputs an ozone mixture 840 (e.g., a mixture of oxygen, ozone and nitrogen) to the process chamber. An ozone sensor 860 is positioned in the path of the ozone mixture 840, in the vicinity of the process chamber. The distance 880 between the ozone sensor 860 and the process chamber 800 is preferably short to provide point of use measurement and controlling. Typically, the distance 880 is preferably less than 1 m, and more preferably less than 10 cm from the process chamber. At that distance, the ozone sensor will have an operating pressure determined by the process chamber, and thus for vacuum processing, the present ozone sensor can be used, since it can operate at low pressure conditions. The ozone sensor can be a standalone ozone sensor, measuring an ozone concentration and providing outputs to the system controller 810.

In some embodiments, the ozone sensor can be a conventional mass flow meter or controller, and the system configuration and software can be modified to provide measuring and controlling capability. For example, an output 865 of the ozone sensor 860 is supplied to the system controller 810, together with the oxygen flow 828 measured from flow controller 825 and the nitrogen flow 838 measured from flow controller 835. The system controller 810 can calculate the ozone concentration based on these inputs. The controller can output a power signal to the ozone generator 870 to regulate the ozone concentration, matching the ozone measurement with a desired ozone level. The system controller 810 can control the flow rates of oxygen and nitrogen, through outputs to the flow controller 825 and 835.

In some embodiments, the present invention discloses methods to configure a vacuum process chamber utilizing ozone generated from an ozone generator accepting an oxygen flow. An exemplary method comprises installing a first mass flow meter in a vicinity of the vacuum process chamber, the mass flow meter coupled to an output flow of the ozone generator; coupling a first output from the first mass flow meter to a system controller, the first output measuring the output flow of the ozone generator; coupling a second output from a second mass flow meter to the system controller, the second output measuring the oxygen flow; and programming the system controller to calculate an ozone concentration from the first and second outputs. The method can further comprise programming the system controller to output a power signal to the ozone generator to achieve a desired ozone concentration.

In some embodiments, the ozone generator further accepts a nitrogen flow. The method then further comprises coupling a third output from a third mass flow meter measuring the nitrogen flow to the system controller; programming the system controller to calculate an ozone concentration from the first, second and third outputs.

In some embodiments, the vacuum process chamber can be configured to perform a deposition utilizing ozone as a process gas, wherein the deposition comprising at least one of atomic layer deposition or chemical vapor deposition.

Figure 9:
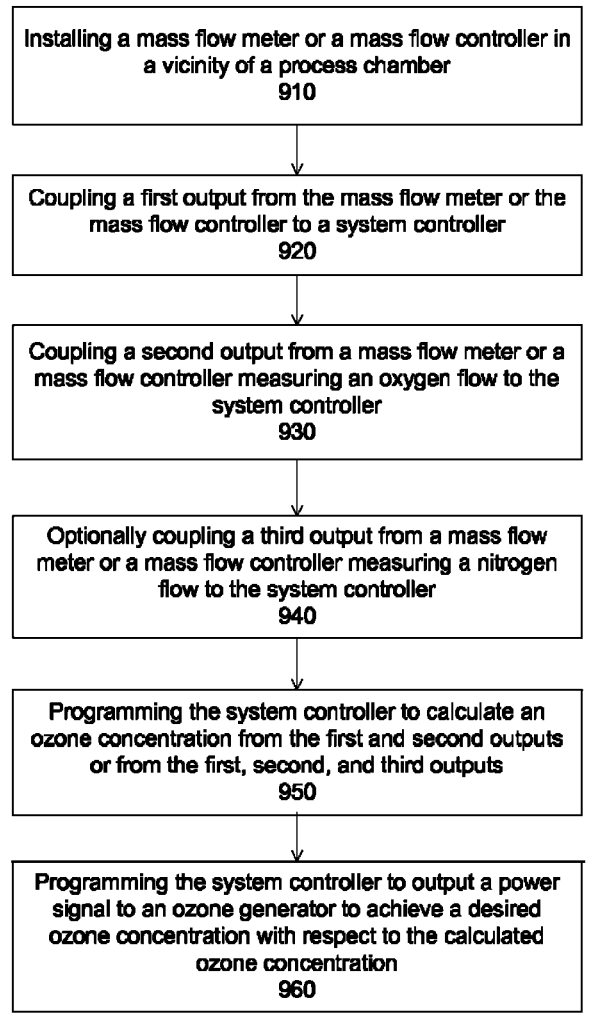
FIG. 9 illustrates an exemplary flowchart for configuring a system using an ozone sensor.

FIG. 9 illustrates an exemplary flowchart for configuring a system using an ozone sensor according to some embodiments of the present invention. In operation 910, a mass flow meter or a mass flow controller is installed in a vicinity of a process chamber. The process chamber is preferably a vacuum processing chamber, and more preferably a vacuum processing chamber utilizing ozone. The mass flow meter or controller can be a conventional mass flow meter or controller, calculating a mass flow rate based on a heat flux or a temperature gradient measurement. In operation 920, a first output from the mass flow meter or the mass flow controller is coupled to a system controller. The system controller can be configured to operate the process chamber, such as transferring a substrate, or controlling gases, power and vacuum to the process chamber. In operation 930, a second output from a mass flow meter or controller measuring an oxygen flow is coupled to the system controller. The oxygen flow can be connected to an ozone generator to generate ozone. Optionally the ozone generator can comprise a nitrogen flow, and a third output from a mass flow meter or controller measuring the nitrogen flow is coupled to the system controller (operation 940). In operation 950, the system controller is programmed to calculate an ozone concentration from the first and second outputs, and optionally from the third output. For example, the system controller can comprise a software programming for operating the process chamber, and the ozone concentration calculation is included in the software programming. In operation 960, the system controller is further programmed to regulate an ozone level setting to the process chamber, comprising outputting a power value to an ozone generator to achieve a desired ozone concentration.

Although the foregoing examples have been described in some detail for purposes of clarity of understanding, the invention is not limited to the details provided. There are many alternative ways of implementing the invention. The disclosed examples are illustrative and not restrictive.

What is claimed is:

1. A method to determine a concentration of ozone in a gas mixture comprising ozone and oxygen, the method comprising:
measuring a total mass flow rate of the gas mixture, wherein measuring the total mass flow rate comprises measuring an oxygen mass flow rate before being converted to the gas mixture of ozone and oxygen;
measuring a thermal property of the gas mixture flow, wherein the thermal property comprises a thermal parameter that has a different value for the first gas compared to that of the second gas;
calculating a concentration of the ozone using the total mass flow rate and the measured thermal property.

2. A method as in claim 1 wherein the thermal property comprises one of a heat flux or a temperature gradient of the gas mixture flow, and the thermal parameter comprises the specific heat.

3. A method as in claim 1 wherein the concentration of ozone is calculated by:
calculating an assumed mass flow rate for ozone using the thermal property of the gas mixture flow and the thermal parameter of oxygen; and
determining the concentration of ozone based on the assumed mass flow rate and the total mass flow rate.

4. A method as in claim 1 wherein the gas mixture further comprises nitrogen with a known mass flow rate, and wherein the concentration of ozone is calculated by using the total mass flow rate of the mixture minus the mass flow rate of nitrogen, and a measured total thermal property for the gas mixture minus a thermal property for nitrogen.

5. A method to control a desired concentration using a concentration determination method as in claim 1, the method further comprising:
delivering a signal representing the concentration of the ozone to an ozone generator; and
regulating the ozone generator to achieve the desired concentration based on the signal.

6. A method as in claim 5, the method regulating the generation of ozone from oxygen.

7. A gas concentration sensor to determine a concentration of ozone in a gas mixture comprising ozone and oxygen, the gas concentration sensor comprising:
an inlet port and an outlet port for the gas mixture flow;
a sensor assembly coupled to the inlet port to measure a thermal property of the gas mixture flow, wherein the thermal property comprises a thermal parameter that has a different value for ozone compared to that of oxygen;

an electrical port to accept a flow signal related to the mass flow rate of the gas mixture;

a controller coupled to the sensor assembly to accept an output of the sensor assembly, the controller further coupled to the electrical port to accept the flow signal, the controller configured to produce a signal related to the concentration of the ozone;

a feedback circuit to provide the concentration signal to an ozone generator; and a power output based on a difference between the concentration signal and a desired concentration to regulate the ozone generator.

8. A gas concentration sensor as in claim 7 wherein the thermal property comprises a heat flux or a temperature gradient of the gas mixture flow, and the thermal parameter comprises the specific heat.

9. A gas concentration sensor as in claim 7 further comprising a mass flow meter to measure the mass flow of the gas mixture flow, and wherein an output of the mass flow meter is coupled to the electrical port.

10. A gas concentration sensor as in claim 7 wherein the mixture further comprises nitrogen with a known mass flow rate;

wherein the flow signal comprises a mass flow rate of ozone and oxygen; and wherein the controller is further configured to convert the thermal property of the total gas mixture to a thermal property of ozone and oxygen.

11. A processing system comprising a gas concentration sensor as in claim 7 and further comprising a process chamber, wherein the outlet port for the gas mixture flow is disposed in a vicinity of the process chamber.

12. A processing system as in claim 11, wherein the controller is further coupled to the process chamber to operate the process chamber.

* * * * *